United States Patent [19]

Tamura et al.

[11] Patent Number: 6,107,323

[45] Date of Patent: *Aug. 22, 2000

[54] PHARMACEUTICAL COMPOSITION

[75] Inventors: Norikazu Tamura, Kobe; Takashi Sohda, Takatsuki; Hitoshi Ikeda, Higashiosaka, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,784

[22] PCT Filed: Apr. 3, 1997

[86] PCT No.: PCT/JP97/01149

§ 371 Date: May 16, 1997

§ 102(e) Date: May 16, 1997

[87] PCT Pub. No.: WO97/37688

PCT Pub. Date: Oct. 16, 1997

[30] Foreign Application Priority Data

Apr. 5, 1996 [JP] Japan ................................ 8-083917

[51] Int. Cl.[7] .......................... A01N 43/78; A01N 43/16; A01N 43/76; A01N 43/50

[52] U.S. Cl. ........................ 514/401; 514/369; 514/456; 514/374

[58] Field of Search ................................ 514/401, 369, 514/456, 374

[56] References Cited

FOREIGN PATENT DOCUMENTS

| | | | |
|---|---|---|---|
| 0 628 313 A1 | 12/1994 | European Pat. Off. | A61K 31/63 |
| 0628313 | 12/1994 | European Pat. Off. | A61K 31/63 |
| 0 749 751 | 12/1996 | European Pat. Off. | A61K 31/41 |
| 0 752 249 | 1/1997 | European Pat. Off. | A61K 45/06 |
| 2 733 911 | 11/1996 | France | A61K 31/495 |
| 95/26188 | 10/1990 | WIPO | A61K 31/41 |
| 91/17771 | 11/1991 | WIPO | A61K 45/06 |
| 92/10097 | 6/1992 | WIPO | A61K 31/41 |
| 94/28924 | 12/1994 | WIPO | A61K 37/64 |
| 95/26724 | 10/1995 | WIPO | A61K 31/415 |
| 97/02032 | 1/1997 | WIPO | A61K 31/40 |

OTHER PUBLICATIONS

K. Shimamoto et al., "Effects of an Angiotensin II Receptor Antagonist, TCV–116, on Insulin Sensitivity in Fructose–Fed Rats," Blood Pressure, 3 (Suppl 5), 1994; pp. 113–116.

*Primary Examiner*—Russell Travers
*Attorney, Agent, or Firm*—Foley & Lardner

[57] ABSTRACT

To provide a pharmaceutical composition which performs a remarkable effect with a relatively decreased dosage, and, with less side effects, a pharmaceutical composition formulated by combination of an angiotensin II-mediated compound or a salt thereof with at least one species of a compound having the activity of increasing insulin-sensitivity, a compound having the activity of improving postprandial hyperglycemia in diabetes mellitus, an indane derivative having the activity of inhibiting angiotensin converting enzyme, a pyridine derivative having the activity of inhibiting HMG-Co A reductase or salts thereof are advantageously employed.

12 Claims, No Drawings

PHARMACEUTICAL COMPOSITION

This Application is a 371 of PCT/JP97/01149, filed Apr. 3, 1997, which claims Priority from Japanese Applicant 8/83917, filed Apr. 5, 1996.

TECHNICAL FIELD

This invention relates to a pharmaceutical composition comprising a compound having angiotensin II antagonistic activity or a salt thereof in combination with at least one species selected from the group consisting of a compound having the activity of increasing insulin-sensitivity, a compound having the activity of improving postprandial hyperglycemia in diabetes mellitus, an indane derivative having the activity of inhibiting angiotensin converting enzyme, a pyridine derivative having the activity of inhibiting HMG-Co A reductase or salts of them, and to the use of the composition.

BACKGROUND ART

Angiotensin II has a strong vasoconstrictive action, aldosterone-synthesizing action and cell-propagating action, which has been considered as one of the mediators of various circulatory diseases. An angiotensin II antagonistic drug suppressing the action of angiotensin, which antagonizes to this angiotensin II at angiotensin II receptor, is useful for the prophylaxis and therapy of circulatory diseases including hypertension, cardiac diseases (e.g. heart failure, myocardial infarction, etc.), cerebral apoplexy, nephritis, arteriosclerosis, etc. And, an angiotensin converting enzyme drug suppresses conversion of angiotensin I to angiotensin II, which is considered, like angiotensin II antagonistic drugs, as useful for the prophylaxis and therapy of circulatory diseases including hypertension, cardiac diseases (e.g. heart failure, myocardial infarction, etc.), cerebral apoplexy, nephritis, arteriosclerosis, etc. However, since angiotensin converting enzyme is the same enzyme as kininase II which destructs kinin, and it has no substrate specificity, it has such an undesirable side effect as depositing inflammatory peptide including kinin and the substance P to cause occurrence of cough.

On the other hand, in the therapy of diabetes mellitus, there has been given treatment with a medicine to improve postprandial hyperglycemia in diabetes mellitus or treatment with a medicine to increase insulin sensitivity for preventing lowering of insulin sensitivity to the intake of glucose in peripheral tissue.

Further, in the therapy of hyperlipemia, a medicine of inhibiting HMG-Co A reductase (3-hydroxy-3-methylglutaryl coenzyme A reductase) is employed to suppress the biosynthesis of cholesterol.

Above all, such diseases as hypertension, abnormal carbohydrate tolerance and abnormal lipid metabolism have been known to be complicated with one another. Especially, hypertension and insulin resistance, or hypertension and arteriosclerosis are considered to aggravate the respective counterpart diseases.

This invention is intended, by combination of a compound having angiotensin II antagonistic action or a salt thereof with a compound having action mechanism other than the above, to perform especially remarkable effects in angiotensin II-mediated diseases, especially hypertension, hyperlipemia, arteriosclerosis and so on, singly or complications of these diseases and to cover up various defects observed in administration of a medicine consisting of a single component.

Circumstances being such as above, the present inventors have actually combined, for the first time, a compound having angiotensin antagonistic activity or a salt thereof, which is the essential component, with at least one species selected from the group consisting of a compound having an insulin sensitivity increasing action, a compound having the activity of improving postprandial hyperglycoplasmia in diabetes mellitus, an indane derivative having the action of inhibiting angiotensin converting enzyme, a pyridine derivative having the action of HMG-Co A reductase or salts thereof, and, as a result, they have found that the co-use performs especially remarkable effects (e.g. in the treatment effect, safety, stability, dose, administration route, method of use, etc.) which were not observed in the administration of the respective compounds singly, and they have conducted further studies to accomplish the present invention.

SUMMARY OF THE INVENTION

More specifically, the present invention relates to (1) a pharmaceutical composition comprising a compound having angiotensin II antagonistic activity or a salt thereof in combination with at least one species selected from the group consisting of a compound having the activity of increasing insulin-sensitivity, a compound having the activity of lowering postprandial hyperglycemia in diabetes mellitus, an indane derivative having the activity of inhibiting angiotensin converting enzyme, a pyridine derivative having the activity of inhibiting HMG-Co A reductase and their salts;

(2) the composition as described in the above (1), which is a prophylactic (preventing) or therapeutic (treating) agent of angiotensin II-mediated diseases;

(3) the composition as described in the above (2), which is directed to the prophylaxis or therapy of circulatory diseases;

(4) the composition as described in the above (2), which is directed to the prophylaxis (prevention) or therapy (treatment) of hypertension, cardiac insufficiency, cerebral apoplexy, ischemic peripheral circulation disturbances, myocardial ischemia, venous insufficiency, progressive cardiac insufficiency after myocardial infarction, diabetic nephropathy, nephritis, glomerulonephritis, arteriosclerosis, angiohypertrophy, vascular hypertrophy or obstruction after percutaneous transluminal coronary angioplasty, vascular reobstruction after bypass surgery, hyperaldosteronism, glomerulosclerosis, renal insufficiency, glaucoma, occular hypertension, hyperlipemia, myocardial infarction, angina pectoris, aneurysm, coronary arteriosclerosis, cerebral arteriosclerosis, peripheral arteriosclerosis, thrombosis, diseases of central nervous system, Alzheimer's disease, deficiency of memory, depression, amnesia, senile dementia, sensory disturbances, multiple system organ failure or scleroderma, or to the prevention or amelioration of anxiety neurosis, catatonia, indisposition or dyspeptic symptoms;

(5) the composition as described in the above (2), which is directed to the prophylaxis or therapy of complications of hypertension;

(6) the composition as described in the above (2), which is directed to the prophylaxis or therapy of arteriosclerosis;

(7) the composition as described in the above (5), which is directed to the prophylaxis or therapy of arteriosclerosis;

(8) the composition as described in the above (1), wherein the compound having angiotensin II antagonistic activity is a compound of the formula:

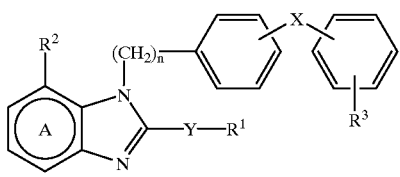

(I)

wherein R¹ stands for H or an optionally substituted hydrocarbon residue; R² stands for an optionally esterified carboxyl group; R³ stands for a group capable of forming anion or a group convertible thereto; X shows that phenylene group and phenyl group are bonded directly or through a spacer having a chain length of 1 to 2 atoms; n denotes 1 or 2; the ring A is a benzene ring optionally having further substituents other than the group shown by R²; and Y stands for a bond, —O—, —S(O)m— (m denotes 0, 1 or 2) or —N(R⁴)— (R⁴ stands for H or an optionally substituted alkyl group);

(9) the composition as described in the above (1), wherein the compound having angiotensin II antagonistic activity is (±)-1-(cyclohexyloxycarbonyloxy)ethyl 2-ethoxy-1-[[2'-(1 H-tetrazol-5-yl)biphenyl-4-yl]methyl]-1 H-benzimidazole-7-carboxylate, 2-ethoxy-1-[[2'-(1 H-tetrazol-5-yl)biphenyl-4-yl]methyl]-1 H-benzimidazole-7-carboxylic acid or 2-ethoxy-1-[[2'-(2,5-dihydro-5-oxo-1,2,4-oxadiazol-3-yl) biphenyl-4-yl]methyl]-1 H-benzimidazole-7-carboxyalic acid;

(10) the composition as described in the above (1), wherein the compound having the activity of increasing insulin-sensitivity is 5-[4-[2-(5-ethyl-2-pyridyl)ethoxy]-benzyl]-2,4-thiazolidinedione or (R)-(±)-5-[3-[4-(2-(2-furyl)-5-methyl-4-oxazolylmethoxyj-3-methoxyphenyl]-propyl]-2,4-oxazolidinedione;

(11) the composition as described in the above (1), wherein the compound having the activity of improving post-prandial hyperglycemia in diabetes mellitus is N-(1,3-dihydroxy-2-propyl)valiolamine;

(12) the composition as described in the above (1), wherein the indane derivative having the activity of inhibiting angiotensin converting enzyme is N-[N-[(S)-1-ethoxy-carbonyl-3-phenylpropyl]-L-alanyl]-N-(indan-2-yl)-glycine;

(13) the composition as described in the above (1), wherein the pyridine derivative having the activity of inhibiting HMG-Co A reductase is (+)-3R,5S-erythro-(E)-7-[4-(4-fluorophenyl)-2,6-diisopropyl-5-methoxymethyl-pyridin-3-yl]-3,5-dihydroxyhept-6-enoic acid [(3R,5S,6E)-7-[4-(p-fluorophenyl)-2,6-diisopropyl-5-(methoxymethyl)-3-pyridyl]-3,5-dihydroxy-6-heptenoic acid];

(14) the composition as described in the above (1), wherein the compound having angiotensin II antagonistic activity is (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate, 2-ethoxy-1-[[2'-(1H-tetrazol-5-yl)biphenyl-4-yl]methyl]-1H-benzimidazole-7-carboxylic acid or 2-ethoxy-1-[[2'-(2,5-dihydro-5-oxo-1,2,4-oxadiazol-3-yl)biphenyl-4-yl]methyl]-1H-benzimidazole-7-carboxylic acid;

the compound having the activity of increasing insulin-sensitivity is 5-[4-[2-(5-ethyl-2-pyridyl)ethoxy]-benzyl]-2,4-thiazolidinedione or (R)-(+)-5-[3-[4-[2-(2-furyl)-5-methyl-4-oxazolylmethoxy]-3-methoxyphenyl]-propyl]-2,4-oxazolidinedione;

the compound having the activity of improving post-prandial hyperglycemia in diabetes mellitus is N-(1,3-dihydroxy-2-propyl)valiolamine;

the indane derivative having the activity of inhibiting angiotensin converting enzyme is N-[N-[(S)-1-ethoxy-carbonyl-3-phenylpropyl]-L-alanyl]-N-(indan-2-yl)-glycine; and the pyridine derivative having the activity of inhibiting HMG-Co A reductase is (+)-3R,5S-erythro-(E)-7-[4-(4-fluorophenyl)-2,6-diisopropyl-5-methoxymethyl-pyridin-3-yl]-3,5-dihydroxyhept-6-enoic acid;

(15) the composition as described in the above (1) comprising the compound having angiotensin II antagonistic activity or a salt thereof in combination with the compound having the activity of increasing insulin-sensitivity or a salt thereof;

(16) the composition as described in the above (1) comprising the compound having angiotensin II antagonistic activity or a salt thereof in combination with the compound having the activity of lowering postprandial hyperglycemia in diabetes mellitus or a salt thereof;

(17) a pharmaceutical composition for the prevention or treatment of hypertension, arteriosclerosis or hyperlipemia comprising (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate or a salt thereof in combination with at least one species selected from the group consisting of 5-[4-[2-(5-ethyl-2-pyridyl)ethoxy]benzyl]-2,4-thiazol-idinedione, (R)-(+)-5-[3-[4-[2-(2-furyl)-5-methyl-4-oxazolylmethoxy]-3-methoxyphenyl]propyl]-2,4-oxazol-idinedione, N-(1,3-dihydroxy-2-propyl)valiolamine, N-[N-[(S)-1-ethoxycarbonyl-3-phenylpropyl]-L-alanyl]-N--(indan-2-yl)glycine, (+)-3R,5S-erythro-(E)-7-[4-(4-fluorophenyl)-2,6-diisopropyl-5-methoxymethylpyridin-3-yl]-3,5-dihydroxyhept-6-enoic acid and their salts;

(18) a pharmaceutical composition for the prevention or treatment of hypertension, arteriosclerosis or hyperlipemia comprising 2-ethoxy-1-[[2'-(1H-tetrazol-5-yl)biphenyl-4-yl]methyl]-1H-benzimidazole-7-carboxylic acid or a salt thereof in combination with at least one species selected from the group consisting of 5-[4-[2-(5-ethyl-2-pyridyl) ethoxy]-benzyl]-2,4-thiazolidine-dione, (R)-(+)-5-[3-[4-[2-(2-furyl)-5-methyl-4-oxazolylmethoxy]-3-methoxyphenyl]-propyl]-2,4-oxazolidinedione, N-(1,3-dihydroxy-2-propyl) valiolamine, N-[N-[(S)-1-ethoxycarbonyl-3-phenylpropyl]-L-alanyl]-N-(indan-2-yl)glycine, (+)-3R,5S-erythro-(E)-7-[4-(4-fluorophenyl)-2,6-diiso-propyl-5-methoxymethylpyridin-3-yl]-3,5-dihydroxyhept-6-enoic acid and their salts;

(19) a pharmaceutical composition for the prevention or treatment of hypertension, arteriosclerosis or hyperlipemia comprising 2-ethoxy-1-[[2'-(2,5-dihydro-5-oxo-1,2,4-oxadiazol-3-yl)biphenyl-4-yl]methyl]-1H-benzimidazole-7-carboxylic acid or a salt thereof in combination with at least one species selected from the group consisting of 5-[4-[2-(5-ethyl-2-pyridyl)ethoxy]benzyl]-2,4-thiazolidinedi-one, (R)-(+)-5-[3-[4-[2-(2-furyl)-5-methyl-4-oxazolyl-methoxy]-3-methoxyphenyl]propyl]-2,4-oxazolidinedione, N-(1,3-dihydroxy-2-propyl)valiolamine, N-[N-[(S)-1-ethoxycarbonyl-3-phenylpropyl]-L-alanyl]-N-(indan-2-yl) glycine, (+)-3R,5S-erythro-(E)-7-[4-(4-fluoro--phenyl)-2,6-diisopropyl-5-methoxymethylpyridin-3-yl]-3,5-dihydroxyhept-6-enoic acid and their salts;

(20) a method for preventing or treating angiotensin II-mediated diseases in a mammal, which comprises administering to said mammal a compound having angiotensin II antagonistic activity or a salt thereof in combination with at least one species selected from the group consisting of a compound having the activity of increasing insulin-sensitivity, a compound having the activity of lowering postprandial hyperglycemia in diabetes mellitus, an indane derivative having the activity of inhibiting angiotensin converting enzyme, a pyridine derivative having the activity of inhibiting HMG-Co A reductase and their salts; and

(21) use of a compound having angiotensin II antagonistic activity or a salt thereof in combination with at least one species selected from the group consisting of a compound having the activity of increasing insulin-sensitivity, a compound having the activity of lowering postprandial hyperglycemia in diabetes mellitus, an indane derivative having the activity of inhibiting angiotensin converting enzyme, a pyridine derivative having the activity of inhibiting HMG-Co A reductase and their salts, for the manufacture of a medicament for preventing or treating angiotensin II-mediated diseases.

DETAILED EXPLANATION OF THE INVENTION

Specific examples of the compound having the angiotensin II antagonistic activity or salts thereof include benzimidazol-7-carboxylic acid derivatives and salts thereof disclosed in, for example, JP-A [Japanese Patent Application Laid-open No.] H4(1992)-9373, EP-A- 425921, JP-A H4(1992)-364171, EP-A-459136 and EP-A- 520423, preferably compounds represented by the following formula (I) or salts thereof (preferably, pharmacologically acceptable salts). Formula (I)

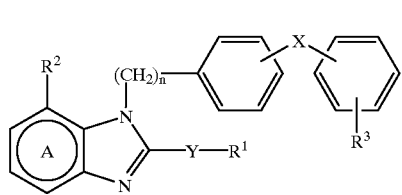

(I)

wherein $R^1$ stands for H or an optionally substituted hydrocarbon residue; $R^2$ stands for an optionally esterified carboxyl group; $R^3$ stands for a group capable of forming anion or a group convertible thereto; X shows that phenylene group and phenyl group are bonded directly or through a spacer having a chain length of 1 to 2 atoms; n denotes 1 or 2; the ring A is a benzene ring optionally having further substituents other than groups shown by $R^2$; and Y stands for a bond, —O—, —S(O)m— (wherein m denotes 0, 1 or 2) or —N($R^4$)— (wherein $R^4$ stands for H or an optionally substituted alkyl group).

In the above formula (I), examples of the hydrocarbon residue shown by $R^1$ include alkyl, alkenyl, alkynyl, cycloalkyl, aryl and aralkyl groups. Among them, alkyl, alkenyl and cycloalkyl groups are preferable.

The alkyl group shown by $R^1$ is a straight chain or branched lower alkyl group having 1 to about 8 carbon atoms, as exemplified by methyl, ethyl, propyl, isopropyl, butyl, isobutyl, sec-butyl, t-butyl, pentyl, i-pentyl, hexyl, heptyl and octyl.

The alkenyl group shown by $R^1$ is a straight chain or branched lower alkenyl group having 2 to about 8 carbon atoms, as exemplified by vinyl, propenyl, 2-butenyl, 3-butenyl, isobutenyl and 2-octenyl.

The alkynyl group shown by $R^1$ is a straight chain or branched lower alkynyl group having 2 to about 8 carbon atoms, as exemplified by ethynyl, 2-propynyl, 2-butynyl, 2-pentynyl and 2-octynyl.

The cycloalkyl group shown by $R^1$ is a lower cycloalkyl group having 3 to about 6 carbon atoms, as exemplified by cyclopropyl, cyclobutyl, cyclopentyl and cyclohexyl.

The above-mentioned alkyl, alkenyl, alkynyl or cycloalkyl group may optionally be substituted with hydroxyl group, an optionally substituted amino group (e.g. amino, N-lower ($C_{1-4}$)alkylamino, N,N-dilower ($C_{1-4}$) alkylamino, etc.), halogen, a lower ($C_{1-4}$) alkoxy group or a lower ($C_{1-4}$) alkylthio group.

The aralkyl group shown by $R^1$ is exemplified by a phenyl-lower ($C_{1-4}$) alkyl such as benzyl, phenethyl, etc. and the aryl group shown by $R^1$ is exemplified by phenyl, etc.

The above-mentioned aralkyl or aryl group may optionally have, on any position of its benzene ring, for example, halogen (e.g. F, Cl, Br, etc.), nitro, an optionally substituted amino group (e.g. amino, N-lower ($C_{1-4}$) alkylamino, N,N-dilower ($C_{1-4}$) alkylamino, etc.), lower ($C_{1-4}$) alkoxy (e.g. methoxy, ethoxy, etc.), lower ($C_{1-4}$) alkylthio (e.g. methylthio, ethylthio, etc.), lower ($C_{1-4}$) alkyl (e.g. methyl, ethyl, etc.), etc.

Among the above-mentioned groups shown by $R^1$, optionally substituted alkyl, alkenyl or cycloalkyl groups [e.g. a lower ($C_{1-5}$) alkyl, lower ($C_{2-5}$) alkenyl or lower ($C_{3-6}$) cycloalkyl group optionally substituted with hydroxyl group, amino group, halogen or a lower ($C_{1-4}$) alkoxy group] are preferable.

Y stands for a bond, —O—, —S(O)m— (wherein m denotes 0, 1 or 2) or —N($R^4$)— (wherein $R^4$ stands for H or an optionally lower alkyl group), preferably a bond, —O—, —S— or —N($R^4$)— [wherein $R^4$ stands for H or a lower ($C_{1-4}$) alkyl (e.g. methyl, ethyl, propyl, isopropyl, butyl, sec-butyl, t-butyl, etc.)].

With respect to the above-mentioned formula (I), the group shown by $R^3$, capable of forming anion (a group having a hydrogen atom capable of leaving as proton), or a group capable of changing thereto, is exemplified by 5- to 7-membered (preferably 5- to 6-membered) monocyclic optionally substituted heterocyclic ring residue which contain one or more of N, S and O (preferably N-containing heterocyclic ring residue having a hydrogen atom capable of leaving as proton) or groups capable of changing thereto in vivo. Such groups include the following:

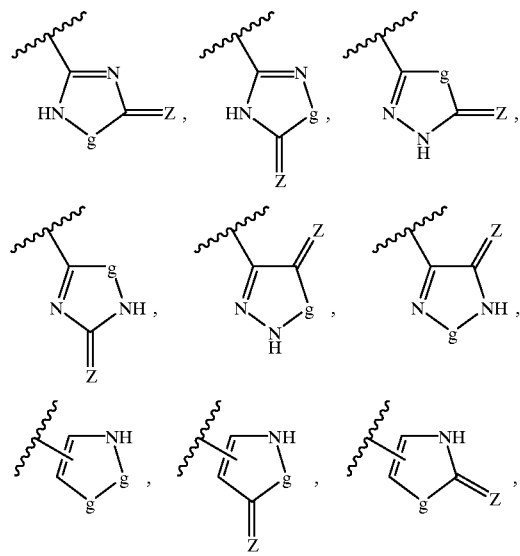

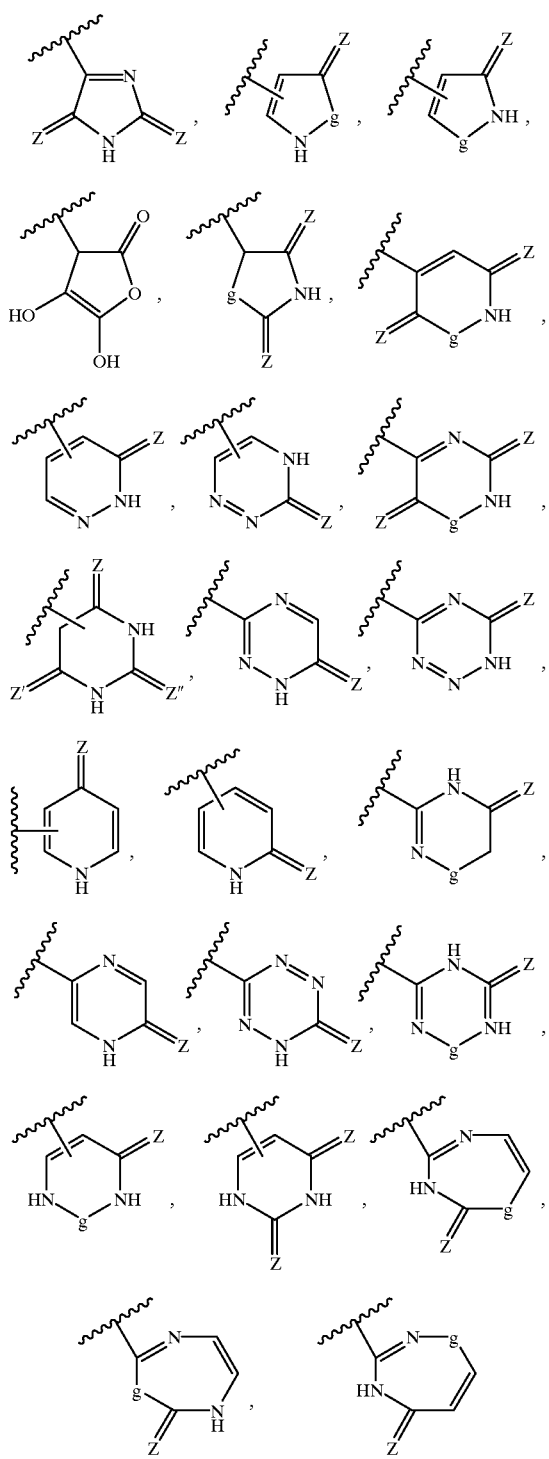

The chemical bond between the group shown by R³ and the partner phenyl group may be a carbon-carbon bond as shown above, or a nitrogen-carbon bond via one of the several nitrogen atoms when the symbol g stands for —NH— in the above formulae. For instance, when R³ is shown by

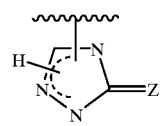

, specific examples include:

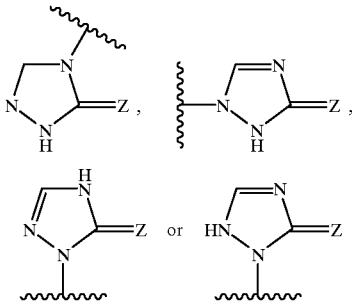

Other examples of R³ bonded through nitrogen atom include:

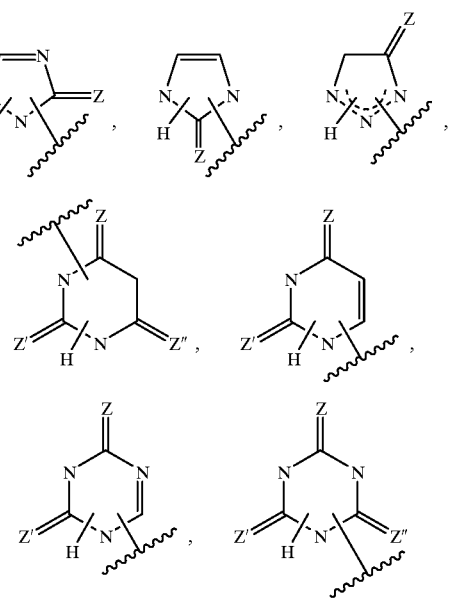

In the above formulae, g stands for

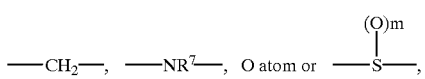

>=Z, >=Z' and >=Z" each stands for a carbonyl group, a thiocarbonyl group or an optionally oxidized sulfur atom (e.g. S, S(O), S(O)₂, etc.; preferably a carbonyl or thiocarbonyl group; more preferably, a carbonyl group); m denotes 0, 1 or 2; R⁷ stands for H or an optionally substituted lower alkyl group (e.g. a lower ($C_{1-4}$) alkyl such as methyl, ethyl, propyl, isopropyl, butyl, sec-butyl and t-butyl).

Preferable examples of R³ include 2,5-dihydro-5-oxo-1, 2,4-oxadiazole ring residue, 2,5-dihydro-5-thioxo-1,2,4-oxadiazole ring residue or 2,5-dihydro-5-oxo-1,2,4- thiadiazole ring residue having —NH or —OH group as proton donor and carbonyl group, thiocarbonyl group or sulfinyl group as proton acceptor simultaneously.

And, while the heterocyclic residue shown by R³ may form a condensed ring by connecting the substituents on the ring, it is preferably a 5- to 6-membered ring, more preferably a 5-membered heterocyclic residue. As R³, groups represented by the formula

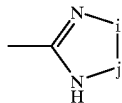

wherein i stands for —O— or —S—; j stands for >C=O, ->C=S or >S(O)m; and m is of the same meaning as defined above (especially, 2,5-dihydro-5-oxo-1,2,4-oxadiazol-3-yl, 2,5-dihydro-5-thioxo-1,2,4-oxadiazol-3-yl or 2,5-dihydro-5-oxo-1,2,4-thiadiazol-3-yl) are preferable. R³ can be substituted at any of the ortho, meta and para position of the phenyl group, most preferably at the ortho position.

In addition, the above-mentioned heterocyclic residue (R³) have the following tautomeric isomers.

For example,

In

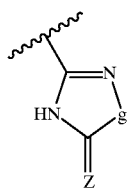

, when Z=O and g=O,

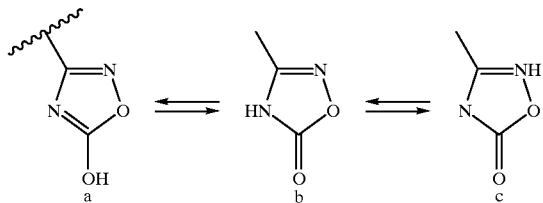

the three tautomeric isomers a, b and c exist. And, the heterocyclic residue represented by the formula

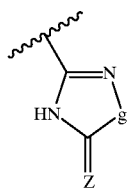

include all of the above-mentioned a, b and c.

Moreover, R³ may be a carboxyl group, tetrazolyl group, trifluoromethanesulfonamide group (—NHSO$_2$CF$_3$), phosphoric acid group, sulfonic acid group, cyano group or lower (C$_{1-4}$) alkoxycarbonyl group; these groups each may be protected with an optionally substituted lower alkyl group or acyl group, and, any group capable of forming an anion biologically or physiologically (e.g. through biological reactions such as oxidation, reduction or hydrolysis caused by enzymes in the body) or chemically, or a group capable of changing thereto is acceptable.

As R³, a tetrazolyl or carboxyl (preferably tetrazolyl) group optionally protected with an optionally substituted lower (C$_{1-4}$) alkyl (e.g. methyl, triphenylmethyl, methoxymethyl, ethoxymethyl, p-methoxybenzyl, p-nitrobenzyl, etc.) or acyl group (e.g. lower (C$_{2-5}$) alkanoyl, benzoyl, etc.) is preferable. R³ can be substituted at any of ortho-, meta- and para- positions, preferably at the ortho-position.

X shows the linkage of phenylene group and phenyl group adjacent to each other directly or through a spacer having a chain length of 1 to 2 atoms (preferably direct linkage). The spacer having a chain length of 1 to 2 atoms may consist of a divalent chain in which the number of atoms composing the straight chain portion is either 1 or 2, and may have a side chain, as exemplified by a lower (C$_{1-4}$) alkylene, —CO—, —O—, —S—, —NH—, —CO—NH—, —O—CH$_2$—, —S—CH$_2$—, —CH=CH—, etc.

The symbol n denotes an integer of 1 or 2 (preferably 1).

The formula represented by the above-mentioned R³, X and n:

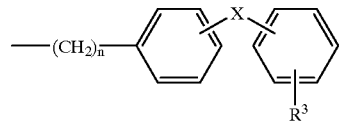

is preferably the following one:

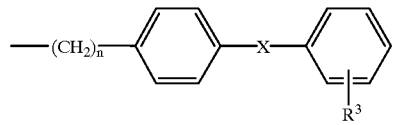

In the formula (I), the optionally esterified carboxyl group shown by R² is exemplified by groups represented by the formula —CO—D [wherein D stands for a hydroxyl group or an optionally substituted alkoxy group {e.g. (i) a lower (C$_{1-6}$) alkoxyl group whose alkyl moiety is optionally substituted with (1) a hydroxyl group, (2) an optionally substituted amino (e.g. amino, N-lower (C$_{1-4}$) alkylamino, N,N-lower (C$_{1-4}$) alkylamino, piperidino, morpholino, etc.), (3) halogen, (4) a lower (C$_{1-6}$) alkoxy, (5) a lower (C$_{1-6}$) alkylthio or (6) an optionally substituted dioxolenyl (e.g. 5-methyl-2-oxo-1,3 -dioxolen-4-yl) group, or (ii) alkoxyl group shown by the formula —O—CH(R⁶)—OCOR⁵ [wherein R⁶ stands for (1) H, (2) a lower (C$_{1-6}$) straight chain or branched alkyl group (e.g. methyl, ethyl, n-propyl, isopropyl, n-butyl, isobutyl, t-butyl, n-pentyl, isopentyl, neopentyl, etc.), (3) a lower (C$_{2-6}$) straight chain or branched alkenyl group (e.g. vinyl, allyl, butenyl, i-butenyl, 2-hexenyl, etc.) or (4) (C$_{3-8}$) cycloalkyl group (e.g. cyclopentyl, cyclohexyl, cycloheptyl, etc.); and R⁵ stands for (1) a lower (C$_{1-6}$) straight chain or branched alkyl group (e.g. methyl, ethyl, n-propyl, isopropyl, n-butyl, isobutyl, sec-butyl, t-butyl, n-pentyl, isopentyl, neopentyl, etc.), (2) a lower (C$_{2-6}$) straight chain or branched alkenyl group (e.g. vinyl, allyl, butenyl, i-butenyl, 2-hexenyl, etc.), (3) a (C$_{3-8}$) cycloalkyl group (e.g. cyclopentyl, cyclohexyl, cycloheptyl, etc.), (4) a lower (C$_{1-3}$) alkyl group substituted with (C$_{3-8}$) cycloalkyl group (e.g. cyclopentyl, cyclohexyi, cycloheptyl, etc.) or an optionally substituted aryl group such as phenyl and naphthyl optionally substituted with halogen, nitro or a lower (C$_{1-4}$) alkyl (e.g. benzyl, p-chlorobenzyl, phenethyl, cyclopentylmethyl, cyclohexylmethyl, etc.), (5) a lower ($C_{2-3}$) alkenyl group optionally substituted with $C_{3-8}$ cycloalkyl or an optionally substituted aryl group such as phenyl and naphthyl optionally substituted with halogen, nitro or a lower ($C_{1-4}$) alkyl (e.g. cinnamyl, etc. having alkenyl moiety such as vinyl, propenyl, allyl and isopropenyl), (6) an optionally substituted aryl group such as phenyl and naphthyl optionally substituted with halogen, nitro or a lower ($C_{1-4}$) alkyl (e.g. phenyl, p-tolyl, naphthyl, etc.), (7) a lower ($C_{1-6}$) straight chain or branched alkoxy group (e.g. methoxy, ethoxy, n-propoxy, isopropoxy, n-butoxy, isobutoxy, sec-butoxy, t-butoxy, n-pentyloxy, isopentyloxy, neopentyloxy, etc.), (8) a lower ($C_{2-8}$) straight chain or branched alkenyloxy group (e.g. allyloxy, isobutenyloxy, etc.), (9) a ($C_{3-8}$) cycloalkyloxy group (e.g. cyclopentyloxy, cyclohexyloxy, cycloheptyloxy, etc.), (10) a lower ($C_{1-3}$) alkoxy group substituted with ($C_{3-8}$) cycloalkyl (e.g. cyclopentyl, cyclohexyl, cycloheptyl, etc.) or an optionally substituted aryl group such as phenyl and naphthyl optionally substituted with halogen, nitro or lower ($C_{1-4}$) alkyl (e.g. benzyloxy, phenethyloxy, cyclohexylmethoxy, etc. having alkoxy moiety such as methoxy, ethoxy, n-propoxy, isopropoxy, etc.), (11) a lower ($C_{2-3}$) lower alkenyloxy group substituted with a $C_{3-8}$ cycloalkyl (e.g. cyclopentyl, cyclohexyl, cycloheptyl, etc.) or with an optionally substituted aryl group such as phenyl and naphthyl optionally substituted with halogen, nitro or lower ($C_{1-4}$) alkyl (e.g. cinnamyloxy, etc. having alkenyloxy moiety such as vinyloxy, propenyloxy, allyloxy, isopropenyloxy, etc.) or (12) an optionally substituted aryloxy group such as phenoxy and naphthoxy optionally substituted with halogen, nitro or lower ($C_{1-4}$) alkyl (e.g. phenoxy, p-nitrophenoxy, naphthoxy, etc.)]}]. The substituent shown by $R^2$ may be a group actually or potentially capable of forming anion [e.g. tetrazolyl group, trifluoromethanesulfonamide group, phosphoric acid group or sulfonic acid group optionally protected with an optionally substituted alkyl (e.g. lower ($C_{1-4}$) alkyl, etc.) or acyl (e.g. lower ($C_{2-5}$) alkanoyl, optionally substituted benzoyl, etc.)].

Examples of the substituent $R^2$ include —COOH and its salts, —COOMe, —COOEt, —COOtBu, —COOPr, pivaloyloxymethoxycarbonyl, 1-(cyclohexyloxycarbonyloxy)ethoxycarbonyl, (5-methyl-2-oxo-1,3-dioxolen-4-yl)methoxycarbonyl, acetoxymethoxycarbonyl, propionyloxymethoxycarbonyl, n-butyryloxymethoxycarbonyl, isobutyryloxymethoxycarbonyl, (1-ethoxycarbonyloxyethoxy)carbonyl, (1-acetoxyethoxy)carbonyl, (1-isobutyryloxyethoxy)carbonyl, cyclohexylcarbonyloxymethoxycarbonyl, benzoyloxymethoxycarbonyl, cinnamyloxycarbonyl and cyclopentylcarbonyloxymethoxycarbonyl. Furthermore, $R^2$ may be any of the groups actually or potentially capable of forming anion (e.g. COO$^-$ or its derivatives) under biologic or physiologic conditions (e.g. oxidation or reduction induced by enzyme present in the living body, or in vivo reaction such as hydrolysis) or chemically. $R^2$ may be carboxyl group or its prodrug. $R^2$ may be a group capable of being biologically or chemically transformed, for example, in vivo to anion.

Among the groups described above as $R^2$, preferable ones include carboxyl, esterified carboxyl (e.g. methyl ester, ethyl ester or an ester formed by binding of a group shown by the formula —O—CH($R^6$)—OCOR$^5$ to carbonyl) and optionally protected tetrazolyl, carboaldehyde and hydroxymethyl.

In the formula (I), ring A may have, in addition to the group shown by $R^2$, further substituents as exemplified by halogen (e.g. F, Cl, Br, etc.), cyano, nitro, lower ($C_{1-4}$) alkyl, lower ($C_{1-4}$) alkoxy, an optionally substituted amino group {e.g. amino, N-lower ($C_{1-4}$) alkylamino (e.g. methylamino, etc.), N,N-di-lower ($C_{1-4}$) alkylamino (e.g. dimethylamino, etc.), N-arylamino (e.g. phenylamino, etc.), alicyclic amino (e.g. morpholino, piperidino, piperazino, N-phenylpiperazino, etc.)}, a group shown by the formula —CO—D' [wherein D' stands for hydroxyl group or a lower ($C_{1-4}$) alkoxy group whose alkyl moiety may optionally be substituted with hydroxyl group, lower ($C_{1-4}$) alkoxy, lower ($C_{2-6}$) alkanoyloxy (e.g. acetoxy, pivaloyloxy, etc.) or lower ($C_{1-6}$) alkoxycarbonyloxy (e.g. chain-like alkoxycarbonyloxy such as methoxycarbonyloxy, ethoxycarbonyloxy, etc. or cyclic alkoxycarbonyloxy such as cyclohexyloxycarbonyloxy)], or a tetrazolyl group, a trifluoromethanesulfonamide group, a phosphoric acid group or a sulfonic acid group which may optionally be protected with lower ($C_{1-4}$)alkyl or acyl (e.g. lower ($C_{2-5}$) alkanoyl, optionally substituted benzoyl, etc.); among them, a lower ($C_{1-4}$) alkyl and halogen are preferable. Of these substituents, one or two may simultaneously be substituted at available positions in the ring.

Among the compounds represented by the formula (I) mentioned above, compounds represented by the formula (I') or salts thereof are preferred:

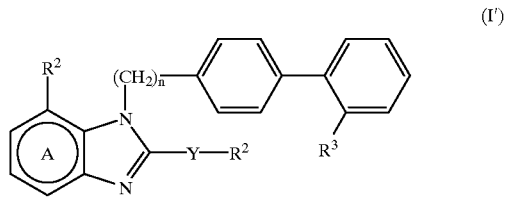

(I')

wherein ring A stands for a benzene ring optionally having further substituents besides groups shown by $R^2$; $R^1$ stands for H or an optionally substituted lower ($C_{1-6}$) alkyl (preferably lower alkyl ($C_{1-4}$) alkyl); Y stands for —O—, —S— or —N(H)—; $R^2$ is a group represented by the formula —CO—D" [wherein D" stands for hydroxyl group, or a lower ($C_{1-4}$) alkoxy whose alkyl moiety is optionally substituted with hydroxyl group, amino, halogen, a lower ($C_{2-6}$) alkanoyloxy (e.g. acetyloxy, pivaloyloxy, etc.), a lower ($C_{4-7}$) cycloalkanoyloxy, (lower ($C_{1-6}$)alkoxy) carbonyloxy (e.g. methoxycarbonyloxy, ethoxycarbonyloxy, etc.), (lower ($C_{3-7}$)cycloalkoxy)carbonyloxy (e.g. cyclohexyloxycarbonyl, etc.) or a lower ($C_{1-4}$)alkoxy; $R^3$ stands for a tetrazolyl, carboxyl group or groups represented by the formula

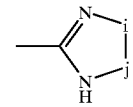

[wherein i stands for —O— or —S—; j stands for >C=O, >C=S or >S(O)m, m denotes 0, 1 or 2] each of which is optionally protected with optionally substituted lower ($C_{1-4}$) alkyl (e.g. methyl, triphenylmethyl, methoxymethyl, acetyloxymethyl, methoxycarbonyloxymethyl, ethoxycarbonyloxymethyl, 1-(cyclohexyloxycarbonyloxy) ethyl, pivaloyloxymethyl, etc.) or an acyl group (e.g. a lower ($C_{2-5}$) alkanoyl, benzoyl, etc.); n denotes 1 or 2 (preferably 1)].

In the formula (I'), as substituents on the optionally substituted, lower alkyl shown by $R^1$, mention is made of a hydroxyl group, an amino group, halogen or a lower ($C_{1-4}$) alkoxy group.

In the formula (I'), as substituents other than those shown by $R^2$ on the ring A, mention is made of halogen (e.g. F, Cl, Br, etc.), lower ($C_{1-4}$) alkyl, lower ($C_{1-4}$) alkoxy, nitro, a group represented by the formula —CO—D' [wherein D' stands for a hydroxyl group or lower ($C_{1-4}$) alkoxy whose alkyl moiety may optionally be substituted with hydroxyl group, lower ($C_{1-4}$) alkoxy, lower ($C_{2-6}$) alkanoyloxy (e.g. acetoxy, pivaloyloxy, etc.) or lower ($C_{1-6}$) alkoxycarbonyloxy (e.g. methoxycarbonyloxy, ethoxycarbonyloxy, cyclohexyloxycarbonyloxy, etc.)] or amino optionally substituted with a lower ($C_{1-4}$) alkyl (preferably lower ($C_{1-4}$) alkyl or halogen). As the ring A, a benzene ring, which has no substituent other than the group represented by the formula $R^2$, is more preferable.

As the salts mentioned above, mention is made of pharmaceutically acceptable ones, as exemplified by a salt with an inorganic base, an organic base, an iorganic acid, an organic acid, or a basic or acidic amino acid. Preferable examples of a salt with an inorganic base include alkali metal salts such as sodium salts, potassium salts, and so on; alkaline earth metal salts such as calcium salts, magnesium salts, and so on; as well as aluminum salts, ammonium salts, etc. Preferable examples of a salt with an organic base include salts with trimethylamine, triethylamine, pyridine, picoline, ethanolamine, diethanolamine, triethanolamine, dicyclohexylamine, N,N'-dibenzylethylenediamine, N-methylmorpholine, etc. Preferable examples of a salt with an inorganic acid include salts with hydrochloric acid, hydrobromic acid, nitric acid, sulfuric acid, phosphoric acid, etc. Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferable examples of a salt with a basic amino acid include salts with arginine, lysine, ornithine, etc. Preferable examples of a salt with an acidic amino acid include salts with aspartic acid, glutamic acid, etc.

Preferable compounds to be employed as the active ingredient of the present invention include those described in the Examples of JP-A H4(1992)-364171/1992, EP-A-459136 and EP-A-520423. Among them, (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate, 2-ethoxy-1-[[2'-(1H-tetrazol-5-yl)biphenyl-4-yl]methyl]-1H-benzimidazole-7-carboxylic acid, 2-ethoxy-1-[[2'-(2,5-dihydro-5-oxo-1,2,4-oxadiazol-3-yl)biphenyl-4-yl]methyl]-1H-benzimidazole-7-carboxylic acid or pharmaceutically acceptable salts thereof are preferable.

The compounds represented by the general formula (I) are disclosed in, for example, JP-A H4(1992)-9373, EP-A-425921, JP-A H4(1992)-364171, EP-A-459136 and EP-A-520423, which can be produced by the methods disclosed in these official publications or methods analogous thereto.

As the compound having the activity of increasing insulin-sensitivity to be used for the present invention or salts thereof, mention is made of a compound having the activity of normalizing the function of the receptor whose insulin-activity is damaged, namely a compound having the activity of releasing the insulin-resistance, or salts thereof. Specific examples of such compounds as above include 2,4-thiazolidinedione, 2,4-oxazolidinedione derivatives or salts thereof described in EP-A-193256, Japan Patent Application No. H7(1995)-284106 (EP-A-710659), JP-A S60(1985)-51189, or known compounds having the activity of increasing insulin-sensitivity, for example, 5-[[3,4-dihydro-2-(phenylmethyl)-2H-1-benzopyran-6-yl]methyl]-2,4-thiazolidinedione (generic name: englitazone); 5-[[4-[3-(5-methyl-2-phenyl-4-oxazolyl)-1-oxopropyl]phenyl]methyl]-2,4-thiazolidinedione (generic name: darglitazone; CP-86325); 5-[2-(5-methyl-2-phenyl-4-oxazolylmethyl) benzofuran-5-ylmethyl]-2,4-oxazolidinedione (CP-92768); 5-(2-naphthalenylsulfonyl)-2,4-thiazolidinedione (AY-31637); 4-[(2-naphthaleneyl)methyl]-3H-1,2,3,5-oxathiadiazol-2-oxide (AY-30711); and 5-[[4-[2-(methyl-2-pyridylamino)ethoxy]phenyl]methyl]-2,4-thiazolinedione (BRL-49653). Preferable compounds include those described as Working Examples in EP-A-193256, Japan Patent Application No. H7(1995)-284106 (EP-A-710659) or JP-A S60(1985)-51189. Among them, 2,4-thiazolidinedione or 2,4-oxazolidinedione derivatives such as 5-[4-[2-(3-ethyl-2-pyridyl)ethoxy]benzyl]-2,4-thiazolidinedione, 5-[4-[2-(5-ethyl-2-pyridyl)ethoxy]benzyl]-2,4-thiazolidinedione, 5-[4-[2-(5-ethyl-2-pyridyl)ethoxy]benzyl]-2,4-thiazolidinedione, 5-[4-[2-(5-ethyl-2-pyridyl)ethoxy]benzyl]-2,4-thiazolidinedione, (R)-(+)-5-[3-[4-[2-(2-furyl)-5-methyl-4-oxazolylmethoxy]-3-methoxyphenyl]propyl]-2,4-oxazolidinedione and CS-045 are preferable, especially, 5-[4-[2-(5-ethyl-2-pyridyl)ethoxy]benzyl]-2,4-thiazolidinedione or (R)-(+)-5-[3-[4-[2-(2-furyl)-5-methyl-4-oxazolylmethoxy]-3-methoxyphenyl]propyl]-2,4-oxazolidinedione is preferable.

Preferable examples of salts of a compound having the activity of increasing (enhancing) insulin-sensitivity include pharmaceutically acceptable salts, which are specifically exemplified by substantially the same ones as pharmaceutically acceptable salts of the above-mentioned compounds having the angiotensin II antagonistic activity.

As the compound having the activity of improving postprandial hyperglycemia in diabetes mellitus or salts thereof to be used in the present invention, mention is made of a compound having the activity of inhibiting α-glucosidase and having the activity of inhibiting a digestive enzyme such as amilase, maltase, α-dextrinase, sucrase and so on to delay the digestion of starch or sucrose, or salts thereof. As examples of them, mention is made of valiolamine derivatives or salts thereof described in EP-A-56194, etc., acarbose or salts thereof described in U.S. Pat. No. 4,062,950, etc. As preferable examples of them, mention is made of compounds described in Examples of EP-A-56194, and, among them, N-(1,3-dihydroxy-2-propyl)valiolamine is preferable.

Preferable examples of salts of a compound having the activity of improving postprandial hyperglycemia in diabetes mellitus include pharmaceutically acceptable salts, which are specifically exemplified by substantially the same ones as pharmaceutically acceptable salts of the above-mentioned compounds having the angiotensin II antagonistic activity.

As indane derivatives having the activity of inhibiting angiotensin converting enzyme or salts thereof to be used in the present invention, mention is made of indane derivatives or salts thereof having the antihypertensive activity by inhibiting angiotensin converting enzyme which converts angiotensin I to angiotensin II. Specific examples of them include indane derivatives or salts thereof described in, for example, JP-A S57(1982)-179141 and EP-A-51391. As preferable compounds, mention is made of those described as Working Examples in JP-A S57(1982)-179141 or EP-A-51391. Among them, N-[N-[(S)-1-ethoxycarbonyl-3-phenylpropyl]-L-alanyl]-N-(indan-2-yl)glycine or salts thereof are preferable, and especially, N-[N-[(S)-1-ethoxycarbonyl-3-phenylpropyl]-L-alanyl]-N-(indan-2-yl) glycine hydrochloride is preferable.

As preferable examples of salts of indane derivatives having the activity of inhibiting angiotensin converting enzyme, mention is made of pharmaceutically acceptable salts. As specific examples of them, mention is made of those which are substantially the same as pharmaceutically acceptable salts of the above-mentioned compound having the angiotensin II antagonistic activity.

In the present invention, a compound having the angiotensin II antagonistic activity or a salt thereof is used in combination with an indane derivative having the activity of inhibiting angiotensin converting enzyme or a salt thereof. In place of the above-mentioned indane derivative having the activity of inhibiting angiotensin converting enzyme, other angiotensin converting enzyme inhibiting agents (e.g. captopril, enalapril, alacepril, ramipril, lisinopril imidapril, etc.) may optionally be used, and, any other antihypertensive agent such as α-blocker, β-blocker, a diuretic or a calcium antagonist may optionally be used in combination with an angiotensin II antagonist.

As the pyridine derivative having the activity of inhibiting HMG-Co A reductase or a salt thereof to be used in the present invention, mention is made of a pyridine derivative having the activity of inhibiting HMG-Co A reductase, which is a rate-limiting enzyme of cholesterol synthesis, or a salt thereof. Specific example of them include pyridine derivatives or salts thereof described in, for example, JP-A H1(1989)-216974, EP-A-325130, JP-A H4(1992)-308573, U.S. Pat. No. 5,177,080, JP-B [Japanese Patent Examined Publication No.] H6(1994)-41448, EP-A-307342, JP-A H1(1989)-121266 and EP-A-306929. As preferable compounds, mention is made of, for example, pyridine derivatives described as Working Examples in these official publications, and, among them, pyridine derivatives described as Working Examples in JP-A H4(1992)-308573 are more preferable, especially preferable one being (+)-3R, 5S-erythro-(E)-7-[4-(4-fluorophenyl)-2,6-diisopropyl-5-methoxymethylpyridin-3-yl]-3,5-dihydroxyhept-6-enoic acid or salts thereof and most preferable one being (+)-3R, 5S-erythro-(E)-7-[4-(4-fluorophenyl)-2,6-diisopropyl-5-methoxymethylpyridin-3-yl]-3,5-dihydroxyhept-6-enoate sodium.

As preferable examples of salts of a pyridine derivative having the activity of inhibiting HMG-Co A reductase, mention is made of pharmaceutically acceptable salts, which are specifically exemplified by substantially the same ones as pharmaceutically acceptable salts of the above-mentioned angiotensin II antagonistic compounds.

In the present invention, an angiotensin II antagonistic compound or a salt thereof is used in combination with a pyridine derivative having the activity of inhibiting HMG-Co A reductase or a salt thereof. And, in place of the above-mentioned pyridine derivatives having the activity of inhibiting HMG-Co A reductase, any other agent of inhibiting HMG-Co A reductase (e.g. pravastatin, simvastatin, lovastatin or fluvastatin may optionally. be employed. And, any other antihyperlipemic drug including an agent of inhibiting squalene synthesis and a fibrate compound having the activity of lowering triglyceride (e.g. bezafibrate) may optionally be used in combination with an angiotensin II antagonistic drug.

In the present invention, a compound having the angiotensin II antagonistic activity or a salt thereof is employed in combination with at least one species of a compound having the activity of increasing insulin-sensitivity, a compound having the activity of improving postprandial hyperglycemia in diabetes mellitus, an indane derivative having the activity of inhibiting angiotensin converting enzyme, a pyridine derivative having the activity of inhibiting HMG-Co A reductase or salts thereof. And, a combination of one or more species of a compound having the activity of increasing insulin-sensitivity, a compound having the activity of improving postprandial hyperglycemia in diabetes mellitus, an indane derivative having the activity of inhibiting angiotensin converting enzyme, a pyridine derivative having the activity of inhibiting HMG-Co A reductase or salts of them may optionally be employed. And, any other drugs (e.g. an antihypertensive drug, an antihyperlipemic drug, etc.) may optionally be combined appropriately with any one of the above compound.

To state further, in the case of using a compound having the angiotensin antagonistic activity or a salt thereof in combination with at least one species of a compound having the activity of increasing insulin-sensitivity, a compound having the activity of improving postprandial hyperglycemia in diabetes mellitus, an indane derivative having the activity of inhibiting angiotensin converting enzyme, a pyridine derivative having the activity of inhibiting HMG-Co A reductase or salts thereof, these drugs can be formulated by mixing individually or simultaneously with pharmaceutically acceptable carriers, excipients, binders, diluents or the like, which can be administered orally or non-orally. In the case of formulating these effective components individually, while thus individually formulated agents can be administered in the form of their mixture prepared by using, for example, a diluent when administered, the individually formulated agents can also be administered separately or simultaneously or with time intervals to the one and same subject. A kit for administering the individually formulated effective components in the form of their mixture prepared by using, for example, a diluent when administered (e.g. a kit for injection which comprises two or more ampoules each comprising a powdery component and a diluent for mixing and dissolving two or more components when administered, etc.), a kit for administering the individually formulated agents simultaneously or with time intervals to the one and same subject (e.g. a kit for tablets to be administered simultaneously or with time intervals, characterized by having two or more tablets each comprising an agent and said tablets being put in one or separate bags and, if necessary, a column to describe time to be administered each agent, etc.) are also included by the pharmaceutical composition of the present invention.

Preferable combinations of the pharmaceutical composition of the present invention are as follows:

(1) a combination of (±)-1-(cyclohexyloxycarbonyloxy) ethyl 2-ethoxy-1-[[2'-(1H-tetrazol-5-yl)biphenyl-4-yl] methyl]-1H-benzimidazole-7-carboxylate or a salt thereof with at least one species of 5-[4-[2-(5-ethyl-2-pyridyl) ethoxy]benzyl]-2,4-thiazolidinedione, (R)-(+)-5-[3-[4-[2-(2-furyl)-5-methyl-4-oxazolylmethoxy]-3-methoxyphenyl] propyl]-2,4-oxazolidinedione, N-(1,3-dihydroxy-2-propyl) valiolamine, N-[N-[(S)-1-ethoxycarbonyl-3-phenylpropyl]-L-alanyl]-N-(indan-2-yl)glycine, (+)-3R,5S-erythro-(E)-7-[4-(4-fluorophenyl)-2,6-diisoprop-yl-5-methoxymethylpyridin-3-yl]-3,5-dihydroxyhept-6-enoic acid or salts thereof;

(2) a combination of 2-ethoxy-1-[[2'-(1H-tetrazol-5-yl) biphenyl-4-yl]methyl]-1H-benzimidazole-7-carboxylic acid or a salt thereof with at least one species of 5-[4-[2-(5-ethyl-2-pyridyl)ethoxy]benzyl]-2,4-thiazolidinedione, (R)-(+)-5-[3-[4-[2-(2-furyl)-5-methyl-4-oxazolylmethoxy]-3-methoxyphenyl]propyl]-2,4-oxazolidinedione, N-(1,3-dihydroxy-2-propyl)valiolamine, N-[N-[(S)-1-ethoxycarbonyl-3-phenylpropyl]-L-alanyl]-N-(indan-2-yl) glycine, (+)-3R,5S-erythro-(E)-7-[4-(4-fluorophenyl)-2,6- diisoprop-yl-5-methoxymethylpyridin-3-yl]-3,5-dihydroxyhept-6-enoic acid or salts thereof, and (3) a combination of 2-ethoxy-1-[[2'-(2,5-dihydro-5-oxo-1,2,4-oxadiazol-3-yl)biphenyl-4-yl]methyl]-1H-benzimidazole-7-carboxylic acid or a salt thereof with at least one species of 5-[4-[2-(5-ethyl-2-pyridyl)ethoxy]benzyl]-2,4-thiazolidinedione, (R)-(+)-5-[3-[4-[2-(2-furyl)-5-methyl-4-oxazolylmethoxy]-3-methoxyphenyl]propyl]-2,4-oxazolidinedione, N-(1,3-dihydroxy-2-propyl)valiolamine, N-[N-[(S)-1-ethoxycarbonyl-3-phenylpropyl]-L-alanyl]-N-(indan-2-yl)glycine, (+)-3R,5S-erythro-(E)-7-[4-(4-fluorophenyl)-2,6-diisopropyl-5-methoxymethylpyridin-yl]-3,5-dihydroxyhept-6-enoic acid or salts thereof. These preferred combinations (1) to (3) are preferably used for the prevention or treatment of hypertension, arteriosclerosis or hyperlipemia, in particular, arteriosclerosis accompanied with hypertension.

Among them, a combination of a compound having the angiotensin II antagonistic activity or a salt thereof with at least one species of a compound having the activity of increasing insulin-sensitivity, a compound having the activity of improving postprandial hyperglycemia in diabetes mellitus or salts of them is preferably used.

The pharmaceutical composition of this invention is used as a prophylactic or therapeutic agent of, for example, angiotensin II-mediated diseases of animals, especially mammals (e.g. man, dog, rabbit, rat, mouse, etc.), as exemplified by circulatory diseases including hypertension, cardiac insufficiency, cerebral apoplexy, ischemic peripheral circulation disturbances, myocardial ischemia, venous insufficiency, progressive cardiac insufficiency after myocardial infarction, diabetic nephropathy, nephritis, glomerulonephritis, arteriosclerosis, angiohypertrophy, vascular hypertrophy or obstruction after percutaneous transluminal coronary angioplasty, vascular reobstruction after bypass surgery, hyperaldosteronism, glomerulosclerosis, renal insufficiency, glaucoma, occular hypertension, hyperlipemia, myocardial infarction, angina pectoris, aneurysm, coronary arteriosclerosis, cerebral arteriosclerosis, peripheral arteriosclerosis, thrombosis; diseases of sensory disturbances including Alzheimer's disease, deficiency of memory, depression, amnesia, senile dementia; diseases of central nervous system including anxiety neurosis, catatonia and indisposition; dyspeptic symptoms, multiple system organ failure, and scleroderma. The pharmaceutical composition of this invention is preferably used as a prophylactic or therapeutic agent for, especially, circulatory diseases including diseases of central nervous system caused by circulatory disturbances. Among the circulatory diseases, for the prophylaxis or therapy of arteriosclerosis and hyperlipemia, use of the pharmaceutical composition of this invention is preferable, especially, use of it for the prophylaxis or therapy of artereiosclerosis is preferable. Further, also for the therapeutic method for lowering cholesterol, the pharmaceutical composition of this invention can be used.

And, the pharmaceutical composition of this invention performs remarkable effects for the prophylaxis or therapy of diseases accompanied with diabetic, obesitic, hyperlipemic or essential hypertension. It is preferably used, especially, for the prophylaxis or therapy of arteriosclerosis accompanied with hypertension.

The pharmaceutical composition of this invention can be administered orally or non-orally in the form of, for example, granules, powdery preparations, dust preparations, tablets, capsules, syrup, emulsions, suppositories (e.g. rectal suppositories and vaginal suppositories), injections (e.g. subcutaneous, intravenous, intramuscular or intraperitoneal injections), instillation, medicines for external application (e.g. preparations to be administered through nasal route, transdermally administrable preparations and ointments), emulsions, elixir, suspensions and solutions. These preparations can be formulated in accordance with per se known methods usually employed in the formulation process. In the present specification, the term "non-orally" includes subcutaneous injection, intravenous injection intramuscular injection, intraperitoneal injection or instillation.

Injectable preparations, for example, sterile injectable aqueous suspensions or oil suspensions can be prepared by known procedures in the relevant fields, using a suitable dispersant or wetting agent and suspending agent. The sterile injections may be in the state of, for example, a solution or a suspension, which is prepared with a non-toxic diluent administrable non-orally, e.g. an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent.

Any non-volatile oil and a fatty acid can be used for this purpose, which include natural or synthetic or semi-synthetic fatty oil or fatty acid, and natural or synthetic or semi-synthetic mono- or di- or tri-glycerides.

Furthermore, additives including a preservative, an isotonizer, a solubilizer, a stabilizer and a pain-soothing agent may adequately be employed.

Rectal suppositories can be prepared by mixing the drug with a suitable non-irritable vehicle, for example, cocoa butter and polyethylene glycols, which are in the solid state at ordinary temperatures, but, in the liquid state at temperatures in intestinal tubes and melt in rectum to release the drug.

As a solid formulation for oral administration, mention is made of powdery preparations, granules, tablets, pills and capsules as referred to in the above. In such formulations as exemplified above, the active components can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as parabens and sorbic acid, an anti-oxidant such as ascorbic acid, α-tocopherol or cysteine, an excipient, a disintegrator, a binder, a thickening agent, a buffer, a sweetener, a flavoring agent, a perfuming agent and a coating agent. Tablets and pills can further be prepared with enteric coating. Examples of liquid preparations for oral administration include pharmaceutically acceptable emulsions, syrups, elixirs, suspensions and solutions, which may contain an inactive diluent, for example, water, which is conventionally employed in the relevant field.

A formulation used for the pharmaceutical composition of this invention preferably comprises, as an effective component, about 0.6 to 39 weight % (more preferably about 0.7 to 27 weight %) of a compound having angiotensin II antagonistic activity or a salt thereof, about 0.06 to 35 weight % (more preferably about 0.6 to 23 weight %) of a compound having the activity of increasing insulin-sensitivity or a salt thereof, about 0.06 to 0.39 weight % (more preferably about 0.06 to 0.24 weight %) of a compound having the activity of improving postprandial hyperglycemia in diabetes mellitus or a salt thereof, about 3 to 46 weight % (more preferably about 3 to 23 weight %) of an indane derivative having the activity of inhibiting angiotensin converting enzyme or a salt thereof and/or about 0.006 to 0.77 weight % (more preferably about 0.006 to 0.39 weight %) of a pyridine derivative having the activity of inhibiting HMG-Co A reductase or salt thereof.

This formulation may be prepared by formulating two or more components individually or simultaneously.

The pharmaceutical composition of this invention is less toxic, which is safely used for animals, especially mammals (e.g. man, dog, rabbit, rat, mouse, etc.) and can be used advantageously for prophylaxis or therapy of angiotensin II-mediated diseases.

The dose of the pharmaceutical composition of this invention is determined in accordance with the dose of individual drugs, and can be selected dependent on the age, body weight, symptom, dose interval, administration routes, type of the formulation, and combination of drugs.

The dose to be administered to a specific patient is dependent on the age, body weight, general health conditions, sex, diet, dose interval, administration routes, excretion rate, combination of drugs and conditions of the diseases then treated, while taking the minimal recommendable clinical dose or these and other necessary factors into consideration.

Typical daily doses of the compositions having various combinations of an angiotensin II antagonistic compound or a salt thereof with at least one species of a compound having the activity of increasing insulin-sensitivity, a compound having the activity of improving postprandial hyperglycemia in diabetes mellitus, an indane derivative having the activity of inhibiting angiotensin converting enzyme, a pyridine derivative having the activity of inhibiting HMG-Co A reductase and salts thereof are within the range of from about 1/50 of the minimal recommendable clinical dose to maximal recommendable dose (preferably minimum recommendable dose, more preferably about 1/2 of minimum recommendable dose) in the case of practical administration of these compounds individually.

For example, in case of the treatment of arteriosclerosis in human adult (body weight: about 60 kg), (±)-1-(cyclohexyloxycarbonyloxy)ethyl 2-ethoxy-[[2'-(1H-tetrazol-5-yl)biphenyl-4-yl]methyl]-1H-benzimidazole-7-carboxylate in a dose ranging from about 1 to 50 mg/patient/day (preferably from about 1 to 35 mg/patient/day) can be effectively combined with, for example, 5-[4-[2-(5-ethyl-2-pyridyl)ethoxy]benzyl]-2,4-thiazolidindione in a dose ranging from about 0.1 to 30 mg/patient/day (preferably from about 2 to 30 mg/patient/day) or N-(1,3-dihydroxy-2-propyl)valiolamine in a dose ranging from about 0.1 to 2 mg/patient/day. Needless to state, while these dosage ranges can be adjusted by a necessary unit base for dividing a daily dose, such doses are decided by taking into consideration the diseases to be treated, conditions of such diseases, the age, body weight, general health conditions, sex and diet of the patient then treated, dose internals, administration routes, excretion rate, combinations of drugs or any other necessary factors into consideration. In the prophylactic or therapeutic agents of this invention, the unit dose is administered once or twice daily (preferably once).

In case of the prevention or treatment of arteriosclerosis of human adult (body weight: about 60 kg), preferred embodiments of the above-mentioned preferred combinations (1) to (3) are shown below:

(1) A tablet comprising about 1 to 50 mg (preferably about 1 to 35 mg) of (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate is orally administered to one and same subject in the form of combination use with a tablet comprising about 0.1 to 45 mg (preferably about 2 to 30 mg) of 5-[4-[2-(5-ethyl-2-pyridyl)ethoxy]benzyl]-2,4-thiazolidinedione, a tablet comprising about 1 to 20 mg (preferably about 1 to 15 mg) of (R)-(+)-5-[3-[4-[2-(2-furyl)-5-methyl-4-oxazolylmethoxy]-3-methoxyphenyl]propyl]-2,4-oxazolidinedione, a tablet comprising about 0.1 to 0.5 mg (preferably about 0.1 to 0.3 mg) of N-(1,3-dihydroxy-2-propyl)valiolamine, a tablet comprising about 5 to 60 mg (preferably about 5 to 30 mg) of N-[N-[(S)-1-ethoxycarbonyl-3-phenylpropyl]-L-alanyl]-N-(indan-2-yl) glycine hydrochloride or a tablet comprising about 0.01 to 1 mg (preferably about 0.01 to 0.5 mg) of (+)-3R,5S-erythro-(E)-7-[4-(4-fluorophenyl)-2,6-diisopropyl-5-methoxymethylpyridin-3-yl]-3,5-dihydroxyhept-6-enoate sodium. Each tablet is preferably administered once a day and may be administered to one and same subject simultaneously or with time intervals of 12 hours or less (preferably 6 hours or less).

(2) A tablet comprising about 1 to 50 mg (preferably about 1 to 35 mg) of 2-ethoxy-1-[[2'-(1H-tetrazol-5-yl)biphenyl-4-yl]methyl]-1H-benzimidazole-7-carboxylic acid is orally administered to one and same subject in the form of combination use with a tablet comprising about 0.1 to 45 mg (preferably about 2 to 30 mg) of 5-[4-[2-(5-ethyl-2-pyridyl)ethoxy]benzyl]-2,4-thiazolidinedione, a tablet comprising about 1 to 20 mg (preferably about 1 to 15 mg) of (R)-(+)-5-[3-[4-[2-(2-furyl)-5-methyl-4-oxazolylmethoxy]-3-methoxyphenyl]-propyl]-2,4-oxazolidinedione, a tablet comprising about 0.1 to 0.5 mg (preferably about 0.1 to 0.3 mg) of N-(1,3-dihydroxy-2-propyl)valiolamine, a tablet comprising about 5 to 60 mg (preferably about 5 to 30 mg) of N-[N-[(S)-1-ethoxycarbonyl-3-phenylpropyl]-L-alanyl]-N-(indan-2-yl)glycine hydrochloride or a tablet comprising about 0.01 to 0.1 mg (preferably about 0.01 to 0.5 mg) of (+)-3R,5S-erythro-(E)-7-[4-(4-fluorophenyl)-2,6-diisopropyl-5-methoxymethylpyridin-3-yl]-3,5-dihydroxyhept-6-enoate sodium. Each tablet is preferably administered once a day and may be administered to one and same subject simultaneously or with time intervals of 12 hours or less (preferably 6 hours or less).

(3) A tablet comprising about 1 to 50 mg (preferably about 1 to 35 mg) of 2-ethoxy-1-[[2'-(2,5-dihydro-5-oxo-1,2,4-oxadiazol-3-yl)biphenyl-4-yl]methyl]-1H-benzimidazole-7-carboxylic acid is orally administered to one and same subject in the form of combination use with a tablet comprising about 0.1 to 45 mg (preferably about 2 to 30 mg) of 5-[4-[2-(5-ethyl-2-pyridyl)ethoxy]benzyl]-2,4-thiazolidinedione, a tablet comprising about 1 to 20 mg (preferably about 1 to 15 mg) of (R)-(+)-5-[3-[4-[2-(2-furyl)-5-methyl-4-oxazolylmethoxy]-3-methoxyphenyl]propyl]-2,4-oxazolidinedione, a tablet comprising about 0.1 to 0.5 mg (preferably about 0.1 to 0.3 mg) of N-(1,3-dihydroxy-2-propyl)valiolamine, a tablet comprising about 5 to 60 mg (preferably about 5 to 30 mg) of N-[N-[(S)-1-ethoxycarbonyl-3-phenylpropyl]-L-alanyl]-N-(indan-2-yl) glycine hydrochloride or a tablet comprising about 0.01 to 1 mg (preferably about 0.01 to 0.5 mg) of (+)-3R,5S-erythro-(E)-7-[4-(4-fluorophenyl)-2,6-diisopropyl-5-methoxymethylpyridin-3-yl]-3,5-dihydroxyhept-6-enate sodium. Each tablet is preferably administered once a day and may be administered to one and same subject simultaneously or with time intervals of 12 hours or less (preferably 6 hours or less).

BEST MODE FOR CARRYING OUT THE INVENTION

By the following formulation examples, the present invention will be illustrated in more detail, and they should not be construed as limiting the invention thereto.

EXAMPLES

Formulation Examples

The pharmaceutical composition (especially the prophylactic or therapeutic agents of angiotensin II-mediated diseases, preferably therapeutic agent for arteriosclerosis of human adult) referred to in this invention, formulated by combination of a compound having the angiotensin II antagonistic activity or a salt thereof with at least one species of a compound having the activity of increasing insulin-sensitivity, a compound having the activity of improving postprandial hyperglycemia in diabetes mellitus, an indane derivative having the activity of inhibiting angiotensin converting enzyme, a pyridine derivative having the activity of inhibiting HMG-Co A reductase or salts thereof can be prepared by, for example, the following prescriptions.

1. Capsules

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) 5-[4-[2-(5-ethyl-2-pyridyl)ethoxy]benzyl]-2,4-thiazolidinedione | 30 mg |
| (3) lactose | 69 mg |
| (4) microcrystalline cellulose | 70 mg |
| (5) magnesium stearate | 10 mg |
| one capsule | 180 mg |

(1), (2), (3), (4) and ½ of (5) were mixed and then granulated. To the granules was added the remainder of (5), and the whole was filled into a gelatin capsule.

2. Tablets

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) 5-[4-[2-(5-ethyl-2-pyridyl)ethoxy]benzyl]-2,4-thiazolidinedione | 30 mg |
| (3) lactose | 66.4 mg |
| (4) corn starch | 20 mg |
| (5) polyethylene glycol | 2.6 mg |
| (6) hydroxypropyl cellulose | 4 mg |
| (7) carmellose calcium | 5.6 mg |
| (8) magnesium stearate | 0.4 mg |
| one tablet | 130 mg |

(1), (2), (3), (4), (5), ⅔ of (6), 2/3 of (7) and ½ of (8) were mixed and then granulated. To the granules were added the remainders of (6), (7) and (8), followed by subjecting the mixture to compression molding.

3. Injections

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) 5-[4-[2-(5-ethyl-2-pyridyl)ethoxy]benzyl]-2,4-thiazolidinedione | 30 mg |
| (3) inositol | 79 mg |
| (4) benzyl alcohol | 20 mg |
| one ampoule | 130 mg |

(1), (2), (3) and (4) were dissolved in distilled water for injection to make the whole volume 2 ml, which was filled into an ampoule. The whole process was conducted under sterile conditions.

4. Capsules

| | |
|---|---|
| (1) 2-ethoxy-1-[[2'-(1H-tetrazol-5-yl)biphenyl-4-yl]-methyl]benzimidazole-7-carboxylic acid | 1 mg |
| (2) (R)-(+)-5-[3-[4-[2-(2-furyl)-5-methyl-4-oxazolylmethoxy]-3-methoxyphenyl]propyl]-2,4-oxazolidinedione | 10 mg |
| (3) lactose | 89 mg |
| (4) microcrystalline cellulose | 70 mg |
| (5) magnesium stearate | 10 mg |
| one capsule | 180 mg |

(1), (2), (3), (4) and ½ of (5) were mixed and then granulated. To the granules was added the remainder of (5), and the whole was filled into a gelatin capsule.

5. Tablets

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) (R)-(+)-5-[3-[4-[2-(2-furyl)-5-methyl-4-oxazolylmethoxy]-3-methoxyphenyl]propyl]-2,4-oxazolidinedione | 10 mg |
| (3) lactose | 86.4 mg |
| (4) corn starch | 20 mg |
| (5) polyethylene glycol | 2.6 mg |
| (6) hydroxypropyl cellulose | 4 mg |
| (7) carmellose calcium | 5.6 mg |
| (8) magnesium stearate | 0.4 mg |
| one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

6. Injections

| | |
|---|---|
| (1) 2-ethoxy-1-[[2'-(1H-tetrazol-5-yl)biphenyl-4-yl]methyl]-1H-benzimidazole-7-carboxylic acid | 1 mg |
| (2) (R)-(+)-5-[3-[4-[2-(2-furyl)-5-methyl-4-oxazolylmethoxy]-3-methoxyphenyl]propyl]-2,4-oxazolidinedione | 10 mg |
| (3) inositol | 99 mg |
| (4) benzyl alcohol | 20 mg |
| one ampoule | 130 mg |

(1), (2), (3) and (4) were dissolved in distilled water for injection to make the whole volume 2 ml, which is filled into an ampoule. The whole process was conducted under sterile conditions.

7. Capsules

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) N-(1,3-dihydroxy-2-propyl)valiolamine | 0.2 mg |
| (3) lactose | 98.8 mg |
| (4) microcrystalline cellulose | 70 mg |
| (5) magnesium stearate | 10 mg |
| one capsule | 180 mg |

(1), (2), (3), (4) and ½ of (5) were mixed and then granulated. To the granules was added the remainder of (5), and the whole was filled into a gelatin capsule.

8. Tablets

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) N-(1,3-dihydroxy-2-propyl)valiolamine | 0.2 mg |
| (3) lactose | 96.2 mg |
| (4) corn starch | 20 mg |
| (5) polyethylene glycol | 2.6 mg |
| (6) hydroxypropyl cellulose | 4 mg |
| (7) carmellose calcium | 5.6 mg |
| (8) magnesium stearate | 0.4 mg |
| one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

9. Injections

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) N-(1,3-dihydroxy-2-propyl)valiolamine | 0.2 mg |
| (3) inositol | 108.8 mg |
| (4) benzyl alcohol | 20 mg |
| one ampoule | 130 mg |

(1), (2), (3) and (4) were dissolved in distilled water for injection to make the whole volume 2 ml, which was filled into an ampoule. The whole process was conducted under sterile conditions.

10. Capsules

| | |
|---|---|
| (1) 2-ethoxy-1-[[2'-(1H-tetrazol-5-yl)biphenyl-4-yl]-methyl]benzimidazole-7-carboxylic acid | 1 mg |
| (2) N-[N-[(S)-1-ethoxycarbonyl-3-phenylpropyl]-L-alanyl]-N-(indan-2-yl)glycine hydrochloride | 10 mg |
| (3) lactose | 89 mg |
| (4) microcrystalline cellulose | 70 mg |
| (5) magnesium stearate | 10 mg |
| one capsule | 180 mg |

(1), (2), (3), (4) and ½ of (5) were mixed and then granulated. To the granules was added the remainder of (5), and the whole was filled into a gelatin capsule.

11. Tablets

| | |
|---|---|
| (1) 2-ethoxy-1-[[2'-(1H-tetrazol-5-yl)biphenyl-4-yl]-methyl]1H-benzimidazole-7-carboxylic acid | 1 mg |
| (2) N-[N-[(S)-1-ethoxycarbonyl-3-phenylpropyl)-L-alanyl]-N-(indan-2-yl)glycine hydrochloride | 10 mg |
| (3) lactose | 86.4 mg |
| (4) corn starch | 20 mg |
| (5) polyethylene glycol | 2.6 mg |
| (6) hydroxypropyl cellulose | 4 mg |
| (7) carmellose calcium | 5.6 mg |
| (8) magnesium stearate | 0.4 mg |
| one tablet | 130 mg |

(1), (2), (3), (4), (5), 2/3 of (6), ⅔ of (7) and ½ of (8) were mixed and then granulated. To the granules were added the remainders of (6), (7) and (8), followed by subjecting the mixture to compression molding.

12. Injections

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) N-[N-[(S)-1-ethoxycarbonyl-3-phenylpropyl]-L-alanyl]-N-(indan-2-yl)glycine hydrochloride | 10 mg |
| (3) inositol | 99 mg |
| (4) benzyl alcohol | 20 mg |
| one ampoule | 130 mg |

(1), (2), (3) and (4) were dissolved in distilled water for injection to make the whole volume 2 ml, which was filled into an ampoule. The whole process was conducted under sterile conditions.

13. Capsules

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) (+)-3R,5S-erythro-(E)-7-[4-(4-fluorophenyl)-2,6-diisopropyl-5-methoxymethylpyridin-3-yl]-3,5-dihydroxyhept-6-enoate sodium | 0.15 mg |
| (3) lactose | 98.85 mg |
| (4) microcrystalline cellulose | 70 mg |
| (5) magnesium stearate | 10 mg |
| one capsule | 180 mg |

(1), (2), (3), (4) and ½ of (5) were mixed and then granulated. To the granules was added the remainder of (5), and the whole was filled into a gelatin capsule.

14. Tablets

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) (+)-3R,5S-erythro-(E)-7-[4-(4-fluorophenyl)-2,6-diisopropyl-5-methoxymethylpyridin-3-yl]-3,5-dihydroxyhept-6-enoate sodium | 0.15 mg |
| (3) lactose | 96.25 mg |
| (4) corn starch | 20 mg |
| (5) polyethylene glycol | 2.6 mg |
| (6) hydroxypropyl cellulose | 4 mg |
| (7) carmellose calcium | 5.6 mg |
| (8) magnesium stearate | 0.4 mg |
| one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

15. Injections

| | |
|---|---|
| (1) 2-ethoxy-1-[[2'-(1H-tetrazol-5-yl)biphenyl-4-yl]-methyl]-1H-benzimidazole-7-carboxylic acid | 1 mg |
| (2) (+)-3R,5S-erythro-(E)-7-[4-(4-fluorophenyl)-2,6-diisopropyl-5-methoxymethylpyridin-3-yl]-3,5-dihydroxyhept-6-enoate sodium | 0.15 mg |
| (3) inositol | 108.85 mg |
| (4) benzyl alcohol | 20 mg |
| one ampoule | 130 mg |

(1), (2), (3) and (4) were dissolved in distilled water for injection to make the whole volume 2 ml, which is filled into an ampoule. The whole process was conducted under sterile conditions.

16. Capsules

| | | |
|---|---|---|
| (1) (±)-1-(cyclohexyloxycarbonyloxy)ethyl 2-ethoxy-1-[[2'-(1H-tetrazol-5-yl)biphenyl-4-yl]-methyl]-1H-benzimidazole-7-carboxylate | | 1 mg |
| (2) 5-[4-[2-(5-ethyl-2-pyridyl)ethoxy]benzyl]-2,4-thiazolidinedione | | 30 mg |
| (3) lactose | | 69 mg |
| (4) microcrystalline cellulose | | 70 mg |
| (5) magnesium stearate | | 10 mg |
| one capsule | | 180 mg |

(1), (2), (3), (4) and ½ of (5) were mixed and then granulated. To the granules was added the remainder of (5), and the whole was filled into a gelatin capsule.

17. Tablets

| | | |
|---|---|---|
| (1) (±)1-(cyclohexyloxycarbonyloxy)ethyl 2-ethoxy-1-[[2'-(1H-tetrazol-5-yl)biphenyl-4-yl]methyl]-1H-benzimidazole-7-carboxylate | | 1 mg |
| (2) 5-[4-[2-(5-ethyl-2-pyridyl)ethoxy]benzyl]-2,4-thiazolidinedione | | 30 mg |
| (3) lactose | | 66.4 mg |
| (4) corn starch | | 20 mg |
| (5) polyethylene glycol | | 2.6 mg |
| (6) hydroxypropyl cellulose | | 4 mg |
| (7) carmellose calcium | | 5.6 mg |
| (8) magnesium stearate | | 0.4 mg |
| one tablet | | 130 mg |

(1), (2), (3), (4), (5), 2/3 of (6), ⅔ of (7) and ½ of (8) were mixed and then granulated. To the granules were added the remainders of (6), (7) and (8), followed by subjecting the mixture to compression molding.

18. Capsules

| | | |
|---|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | | 1 mg |
| (2) (R)-(+)-5-[3-[4-[2-(2-furyl)-5-methyl-4-oxazolylmethoxy]-3-methoxyphenyl]propyl]-2,4-oxazolidinedione | | 10 mg |
| (3) lactose | | 89 mg |
| (4) microcrystalline cellulose | | 70 mg |
| (5) magnesium stearate | | 10 mg |
| one capsule | | 180 mg |

(1), (2), (3), (4) and ½ of (5) were mixed and then granulated. To the granules was added the remainder of (5), and the whole was filled into a gelatin capsule.

19. Tablets

| | | |
|---|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | | 1 mg |
| (2) (R)-(+)-5-[3-[4-[2-(2-furyl)-5-methyl-4-oxazolylmethoxy]-3-methoxyphenyl]propyl]-2,4-oxazolidinedione | | 10 mg |
| (3) lactose | | 86.4 mg |
| (4) corn starch | | 20 mg |
| (5) polyethylene glycol | | 2.6 mg |
| (6) hydroxypropyl cellulose | | 4 mg |
| (7) carmellose calcium | | 5.6 mg |
| (8) magnesium stearate | | 0.4 mg |
| one tablet | | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

20. Capsules

| | | |
|---|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | | 1 mg |
| (2) N-(1,3-dihydroxy-2-propyl)valiolamine | | 0.2 mg |
| (3) lactose | | 98.8 mg |
| (4) microcrystalline cellulose | | 70 mg |
| (5) magnesium stearate | | 10 mg |
| one capsule | | 180 mg |

(1), (2), (3), (4) and ½ of (5) were mixed and then granulated. To the granules was added the remainder of (5), and the whole was filled into a gelatin capsule.

21. Tablets

| | | |
|---|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | | 1 mg |
| (2) N-(1,3-dihydroxy-2-propyl)valiolamine | | 0.2 mg |
| (3) lactose | | 96.2 mg |
| (4) corn starch | | 20 mg |
| (5) polyethylene glycol | | 2.6 mg |
| (6) hydroxypropyl cellulose | | 4 mg |
| (7) carmellose calcium | | 5.6 mg |
| (8) magnesium stearate | | 0.4 mg |
| one tablet | | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compressive molding.

22. Capsules

| | | |
|---|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | | 1 mg |
| (2) N-[N-[(S)-1-ethoxycarbonyl-3-phenylpropyl]-L-alanyl-N-(indan-2-yl)glycine hydrochloride | | 10 mg |
| (3) lactose | | 89 mg |
| (4) microcrystalline cellulose | | 70 mg |
| (5) magnesium stearate | | 10 mg |
| one capsule | | 180 mg |

(1), (2), (3), (4) and ½ of (5) were mixed and then granulated. To the granules was added the remainder of (5), and the whole was filled into a gelatin capsule.

23. Tablets

| | | |
|---|---|---|
| (1) (±)-1-(cyclohexyloxycarbonyloxy)ethyl 2-ethoxy-1-[[2'-(1H-tetrazol-5-yl)biphenyl-4-yl]-1H-benzimidazole-7-carboxylate | | 1 mg |
| (2) N-[N-[(S)-1-ethoxycarbonyl-3-phenylpropyl]-L-alanyl]-N-(indan-2-yl)glycine hydrochloride | | 10 mg |
| (3) lactose | | 86.4 mg |
| (4) corn starch | | 20 mg |
| (5) polyethylene glycol | | 2.6 mg |
| (6) hydroxypropyl cellulose | | 4 mg |
| (7) carmellose calcium | | 5.6 mg |
| (8) magnesium stearate | | 0.4 mg |
| one tablet | | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

24. Capsules

| | | |
|---|---|---|
| (1) | (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 1 mg |
| (2) | (+)-3R,5S-erythro-(E)-7-[4-(4-fluorophenyl)-2,6-diisopropyl-5-methoxymethylpyridin-3-yl]-3,5-dihydroxyhept-6-enoate sodium | 0.15 mg |
| (3) | lactose | 98.85 mg |
| (4) | microcrystalline cellulose | 70 mg |
| (5) | magnesium stearate | 10 mg |
| | one capsule | 180 mg |

(1), (2), (3), (4) and ½ of (5) were mixed and then granulated. To the granules was added the remainder of (5), and the whole was filled into a gelatin capsule.

25. Tablets

| | | |
|---|---|---|
| (1) | (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 1 mg |
| (2) | (+)-3R,5S-erythro-(E)-7-[4-(4-fluorophenyl)-2,6-diisopropyl-5-methoxymethylpyridin-3-yl]-3,5-dihydroxyhept-6-enoate sodium | 0.15 mg |
| (3) | lactose | 96.25 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

26. Capsules

| | | |
|---|---|---|
| (1) | 2-ethoxy-1-[[2'-(2,5-dihydro-5-oxo-1,2,4-oxadiazol-3-yl)biphenyl-4-yl]methyl]-1H-benzimidazole-7-carboxylic acid | 1 mg |
| (2) | 5-[4-[2-(5-ethyl-2-pyridyl)ethoxy]benzyl]-2,4-thiazolidinedione | 30 mg |
| (3) | lactose | 69 mg |
| (4) | microcrystalline cellulose | 70 mg |
| (5) | magnesium stearate | 10 mg |
| | one capsule | 180 mg |

(1), (2), (3), (4) and ½ of (5) were mixed and then granulated. To the granules was added the remainder of (5), and the whole was filled into a gelatin capsule.

27. Tablets

| | | |
|---|---|---|
| (1) | 2-ethoxy-1-[[2'-(2,5-dihydro-5-oxo-1,2,4-oxadiazol-3-yl)biphenyl-4-yl]methyl]-1H-benzimidazole-7-carboxylic acid | 1 mg |
| (2) | 5-[4-[2-(5-ethyl-2-pyridyl)ethoxy]benzyl]-2,4-thiazolidinedione | 30 mg |
| (3) | lactose | 66.4 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

28. Capsules

| | | |
|---|---|---|
| (1) | 2-ethoxy-1-[[2'-(2,5-dihydro-5-oxo-1,2,4-oxadiazol-3-yl)biphenyl-4-yl]methyl]-1H-benzimidazole-7-carboxylic acid | 1 mg |
| (2) | (R)-(+)-5-[3-[4-[2-(2-furyl)-5-methyl-4-oxazolylmethoxy]-3-methoxyphenyl]propyl]-2,4-oxazolidinedione | 10 mg |
| (3) | lactose | 89 mg |
| (4) | microcrystalline cellulose | 70 mg |
| (5) | magnesium stearate | 10 mg |
| | one capsule | 180 mg |

(1), (2), (3), (4) and ½ of (5) were mixed and then granulated. To the granules was added the remainder of (5), and the whole was filled into a gelatin capsule.

29. Tablets

| | | |
|---|---|---|
| (1) | 2-ethoxy-1-[[2'-(2,5-dihydro-5-oxo-1,2,4-oxadiazol-3-yl)biphenyl-4-yl]methyl]-1H-benzimidazole-7-carboxylic acid | 1 mg |
| (2) | (R)-(+)-5-[3-[4-[2-(2-furyl)-5-methyl-4-oxazolylmethoxy]-3-methoxyphenyl]propyl]-2,4-oxazolidinedione | 10 mg |
| (3) | lactose | 86.4 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.45 mg |
| | one tablet | 130 mg |

(1), (2), (3), (4), (5) ⅔ of (6), ⅔ of (7) and ½ of (8) were mixed and then granulated. To the granules were added the remainders of (6), (7) and (8), followed by subjecting the mixture to compression molding.

30. Capsules

| | | |
|---|---|---|
| (1) | 2-ethoxy-1-[[2'-(2,5-dihydro-5-oxo-1,2,4-oxadiazol-3-yl)biphenyl-4-yl]methyl]-1H-benzimidazole-7-carboxylic acid | 1 mg |
| (2) | N-(1,3-dihydroxy-2-propyl)valiolamine | 0.2 mg |
| (3) | lactose | 98.8 mg |
| (4) | microcrystalline cellulose | 70 mg |
| (5) | magnesium stearate | 10 mg |
| | one capsule | 180 mg |

(1), (2), (3), (4) and ½ of (5) were mixed and then granulated. To the granules was added the remainder of (5), and the whole was filled into a gelatin capsule,

31. Tablets

| | | |
|---|---|---|
| (1) | 2-ethoxy-1-[[2'-(2,5-dihydro-5-oxo-1,2,4-oxadiazol-3-yl)biphenyl-4-yl]methyl]-1H-benzimidazole-7-carboxylic acid | 1 mg |

-continued

| | | |
|---|---|---|
| (2) N-(1,3-dihydroxy-2-propyl)valiolamine | 0.2 | mg |
| (3) lactose | 96.2 | mg |
| (4) corn starch | 20 | mg |
| (5) polyethylene glycol | 2.6 | mg |
| (6) hydroxypropyl cellulose | 4 | mg |
| (7) carmellose calcium | 5.6 | mg |
| (8) magnesium stearate | 0.4 | mg |
| one tablet | 130 | mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

32. Capsules

| | | |
|---|---|---|
| (1) 2-ethoxy-1-[[2'-(2,5-dihydro-5-oxo-1,2,4-oxadiazol-3-yl)biphenyl-4-yl]methyl]-1H-benzimidazole-7-carboxylic acid | 1 | mg |
| (2) N-[N-[(S)-1-ethoxycarbonyl-3-phenylpropyl]-L-alanyl]-N-(indan-2-yl)glycine hydrochloride | 10 | mg |
| (3) lactose | 89 | mg |
| (4) microcrystalline cellulose | 70 | mg |
| (5) magnesium stearate | 10 | mg |
| one capsule | 180 | mg |

(1), (2), (3), (4) and ½ of (5) were mixed and then granulated. To the granules was added the remainder of (5), and the whole was filled into a gelatin capsule.

33. Tablets

| | | |
|---|---|---|
| (1) 2-ethoxy-1-[[2'-(2,5-dihydro-5-oxo-1,2,4-oxadiazol-3-yl)biphenyl-4-yl]methyl]-1H-benzimidazole-7-carboxylic acid | 1 | mg |
| (2) N-[N-[(S)-1-ethoxycarbonyl-3-phenylpropyl]-L-alanyl]-N-(indan-2-yl)glycine hydrochloride | 10 | mg |
| (3) lactose | 86.4 | mg |
| (4) corn starch | 20 | mg |
| (5) polyethylene glycol | 2.6 | mg |
| (6) hydroxypropyl cellulose | 4 | mg |
| (7) carmellose calcium | 5.6 | mg |
| (8) magnesium stearate | 0.4 | mg |
| one tablet | 130 | mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

34. Capsules

| | | |
|---|---|---|
| (1) 2-ethoxy-1-[[2'-(2,5-dihydro-5-oxo-1,2,4-oxadiazol-3-yl)biphenyl-4-yl]methyl]-1H-benzimidazole-7-carboxylic acid | 1 | mg |
| (2) (+)-3R,5S-erythro-(E)-7-[4-(4-fluorophenyl)-2,6-diisopropyl-5-methoxymethylpyridin-3-yl]-3,5-dihydroxyhept-6-enoate sodium | 0.15 | mg |
| (3) lactose | 98.85 | mg |
| (4) microcrystalline cellulose | 70 | mg |
| (5) magnesium stearate | 10 | mg |
| one capsule | 180 | mg |

(1), (2), (3), (4) and ½ of (5) were mixed and then granulated. To the granules was added the remainder of (5), and the whole was filled into a gelatin capsule.

35. Tablets

| | | |
|---|---|---|
| (1) 2-ethoxy-1-[[2'-(2,5-dihydro-5-oxo-1,2,4-oxadiazol-3-yl)biphenyl-4-yl]methyl]-1H-benzimidazole-7-carboxylic acid | 1 | mg |
| (2) (+)-3R,5S-erythro-(E)-7-[4-(4-fluorophenyl)-2,6-diisopropyl-5-methoxymethylpyridin-3-yl]-3,5-dihydroxyhept-6-enoate sodium | 0.15 | mg |
| (3) lactose | 96.25 | mg |
| (4) corn starch | 20 | mg |
| (5) polyethylene glycol | 2.6 | mg |
| (6) hydroxypropyl cellulose | 4 | mg |
| (7) carmellose calcium | 5.6 | mg |
| (8) magnesium stearate | 0.4 | mg |
| one tablet | 130 | mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

INDUSTRIAL APPLICABILITY

The pharmaceutical composition of this invention formulated by combination of an angiotensin II antagonistic compound or a salt thereof with at least one species of a compound having the activity of increasing insulin-sensitivity, a compound having the activity of improving postprandial hyperglycemia in diabetes mellitus, an indane derivative having the activity of inhibiting angiotensin converting enzyme, a pyridine derivative having the activity of inhibiting HMG-Co A reductase or salts thereof serves to decrease remarkably the dosages of the individual effective components, and, as a result, suppresses undesirable side effects observed in the case of administering the respective compounds singly, and can be advantageously used as a prophylactic or therapeutic agent of angiotensin II-mediated diseases, especially arteriosclerosis or arteriosclerosis having hypertension as a complication.

What is claimed is:

1. A method for preventing or treating angiotensin II-mediated diseases in a mammal, which comprises administering to said mammal an effective amount of a compound having angiotensin II antagonistic activity or a salt thereof in combination with an effective amount of a compound having the activity of increasing insulin-sensitivity or a salt thereof.

2. The method as claimed in claim 1, wherein said diseases are circulatory diseases.

3. The method as claimed in claim 1, wherein said method is directed to the prevention or treatment of hypertension, cardiac insufficiency, cerebral apoplexy, ischemic peripheral circulation disturbances, myocardial ischemia, venous insufficiency, progressive cardiac insufficiency after myocardial infarction, diabetic nephropathy, nephritis, glomerulonephritis, arteriosclerosis, angiohypertrophy, vascular hypertrophy or obstruction after percutaneous transluminal coronary angioplasty, vascular reobstruction after bypass surgery, hyperaldosteronism, glomerulosclerosis, renal insufficiency, glaucoma, occular hypertension, hyperlipemia, myocardial infarction, angina pectoris, aneurysm, coronary arteriosclerosis, cerebral arteriosclerosis, peripheral arteriosclerosis, thrombosis, diseases of central nervous system, Alzheimer's disease, deficiency of memory, depression, amnesia, senile dementia, sensory disturbances, multiple system organ failure or scleroderma, or to the prevention or amelioration of anxiety neurosis, catatonia, indisposition or dyspeptic symptoms.

4. The method as claimed in claim 1, wherein said method is directed to the prevention or treatment of complications of hypertension.

5. The method as claimed in claim 1, wherein said method is directed to the prevention or treatment of arteriosclerosis.

6. The composition as claimed in claim 4, which is directed to the prevention or treatment of arteriosclerosis.

7. The method as claimed in claim 1, wherein the compound having angiotensin II antagonistic activity is a compound of the formula:

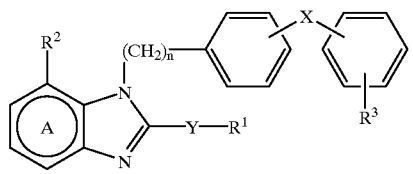

(I)

wherein $R^1$ stands for H or an optionally substituted hydrocarbon residue; $R^2$ stands for an optionally esterified carboxyl group; $R^3$ stands for a group capable of forming anion or a group convertible thereto; X shows that phenylene group and phenyl group are bonded directly or through a spacer having a chain length of 1 to 2 atoms; n denotes 1 or 2; the ring A is a benzene ring optionally having further substituents other than the group shown by $R^2$; and Y stands for a bond, —O—,—S(O)m— (m denotes 0, 1 or 2) or —N($R^4$)—($R^4$ stands for H or an optionally substituted alkyl group).

8. The method as claimed in claim 1, wherein the compound having angiotensin II antagonistic activity is (±)-1-(cyclohexyloxycarbonyloxy)ethyl 2-ethoxy-1-[[2'-(1H-tetrazol-5-yl)biphenyl-4-yl] methyl]- 1 H-benzimidazole-7-carboxylate, 2-ethoxy- 1-[[2'-(1H-tetrazol-5-yl)biphenyl-4-yl] methyl ]-1H-benzimidazole-7-carboxylic acid or 2-ethoxy-1 -[[2'-(2,5-dihydro-5-oxo- 1,2, 4-oxadiazol-3-yl )biphenyl-4-yl ]methyl ]-1H-benzimidazole-7-carboxylic acid.

9. The method as claimed in claim 1, wherein the compound having the activity of increasing insulin-sensitivity is 5-[4-[2-(5-ethyl-2-pyridyl)ethoxy]benzyl]-2,4-thiazolidinedione or (R)-(+)-5-[3-[4-[2-(2-furyl)-5-methyl-4-oxazolylmethoxy]-3-methoxyphenyl]propyl]-2,4-oxazolidinedione.

10. A method as claimed in claim 1, wherein said method is for the prevention or treatment of hypertension, arteriosclerosis or hyperlipemia and which said method comprises administering an effective amount of (±)-1-(cyclohexyloxycarbonyloxy)ethyl 2-ethoxy-1-[[2'-(1H-tetrazol-5-yl)biphenyl-4-yl ]methyl ]-1H-benzimidazole-7-carboxylate or a salt thereof in combination with an effective amount of 5-[4-[2-(5-ethyl-2-pyridyl)ethoxy]benzyl]-2,4-thiazolidinedione or (R)-(+)-5-[3-[4-[2-(2-furyl)-5-methyl-4-oxazolylmethoxy]-3-methoxyphenyl]propyl]-2,4-oxazolidinedione.

11. A method as claimed in claim 1, wherein said method is for the prevention or treatment of hypertension, arteriosclerosis or hyperlipemia and which said method comprises administering an effective amount of 2-ethoxy-1-[[2'-(1H-tetrazol-5-yl)biphenyl-4-yl]methyl]- 1H-benzimidazole-7-carboxylic acid or a salt thereof in combination with an effective amount of 5-[4-[2-(5-ethyl-2-pyridyl) ethoxylbenzyl]-2,4-thiazolidinedione or (R)-(+)-5-[3-[4- [2-(2-furyl)-5-methyl-4-oxazolylmethoxy]-3-methoxyphenyl] propyl]-2,4-oxazolidinedione.

12. A method as claimed in claim 1, wherein said method is for the prevention or treatment of hypertension, arteriosclerosis or hyperlipemia and which said method comprises administering an effective amount of 2-ethoxy-1-[[2'-(2,5-dihydro-5-oxo- 1,2 ,4-oxadiazol-3-yl)biphenyl-4-yl] methyl]-1H-benzimidazole-7-carboxylic acid or a salt thereof in combination with an effective amount of 5-[4-[2-5-ethyl-2-pyridyl)ethoxy]benzyl]-2,4-thiazolidinedione or (R)-(+)-5-[3-[4-[2-(2-furyl)-5 -methyl-4-oxazolylmethoxy] -3-methoxyphenyl]propyl] -2 ,4-oxazolidinedione.

* * * * *